US012733619B2

(12) United States Patent
Christensen et al.

(10) Patent No.: US 12,733,619 B2
(45) Date of Patent: Sep. 15, 2026

(54) DETERMINATION OF HAPTOGLOBIN QUANTITY IN MILK

(71) Applicant: DELAVAL HOLDING AB, Tumba (SE)

(72) Inventors: John M Christensen, Tumba (SE); Claus Dallerup Rasmussen, Tumba (SE); Camilla Dooleweerdt Rasmussen, Tumba (SE); Jonas Trier Hald, Tumba (SE)

(73) Assignee: DeLaval Holding AB, Tumba (SE)

( * ) Notice: Subject to any disclaimer, the term of this patent is extended or adjusted under 35 U.S.C. 154(b) by 371 days.

(21) Appl. No.: 18/563,772

(22) PCT Filed: May 18, 2022

(86) PCT No.: PCT/SE2022/050484

§ 371 (c)(1),
(2) Date: Nov. 22, 2023

(87) PCT Pub. No.: WO2022/250592

PCT Pub. Date: Dec. 1, 2022

(65) Prior Publication Data

US 2024/0251747 A1 Aug. 1, 2024

(30) Foreign Application Priority Data

May 24, 2021 (SE) .................................... 2150655-5

(51) Int. Cl.

*A01J 5/013* (2006.01)
*G01N 33/04* (2006.01)

(52) U.S. Cl.

CPC .......... *A01J 5/0131* (2013.01); *A01J 5/0135* (2013.01); *G01N 33/04* (2013.01)

(58) Field of Classification Search

CPC ........ A01J 5/0131; A01J 5/0135; G01N 33/04
See application file for complete search history.

(56) References Cited

U.S. PATENT DOCUMENTS 5,047,351 A 9/1991 Makiuchi et al.
12,295,344 B2 * 5/2025 Christensen .......... A01J 5/0131
(Continued)

FOREIGN PATENT DOCUMENTS

WO 2013131052 A1 9/2013
WO 2020251457 A1 12/2020
WO 2020251460 A1 12/2020

OTHER PUBLICATIONS

Maria Akerstedt et al. "Biosensor array for determination of haptoglobin in bovine milk" 2006, Journal of Dairy Research 73 pages 299-305 (Year: 2006).*

(Continued)

*Primary Examiner* — Gertrude Arthur Jeanglaude
(74) *Attorney, Agent, or Firm* — NIXON & VANDERHYE

(57) ABSTRACT

A milking arrangement includes a milking machine for milking an animal, where the milking arrangement includes an analysing unit configured to determining a value of haptoglobin quantity in a milk sample taken from milk harvest by the milking machine. The analysing unit including a haptoglobin sensor device configured to provide a value of haptoglobin quantity in the milk sample.

20 Claims, 6 Drawing Sheets

(56) References Cited

U.S. PATENT DOCUMENTS

| | | | | |
|---|---|---|---|---|
| 2014/0141986 A1* | 5/2014 | Spetzler | C12Q 1/6886 | 435/7.1 |
| 2015/0301058 A1* | 10/2015 | Schettini | G01N 33/5076 | 424/193.1 |
| 2018/0180632 A1 | 6/2018 | Lehmann et al. | | |

OTHER PUBLICATIONS

N. Brady, et al., "Development of a lateral flow point of care test for the rapid detection and measurement of haptoglobin in bovine milk", Proceedings of the British Mastitis Conference 2016; Nov. 2, 2016, Worcester, Jan. 1, 2016, pp. 69-70 (2 pages).

Dmitriy V. Sotnikov, et al., "Development of mathematical models of lateral flow membrane bioanalytical systems and characterization of the regularities of their functioning", AIP Conference Proceedings 2216, 060002, published Apr. 1, 2020, 6 pages.

Search Report for SE Application No. 2150655-5 mailed Feb. 4, 2022, 2 pages.

International Search Report for PCT/SE2022/050484 mailed Nov. 14, 2022, 4 pages.

Written Opinion of the ISA for PCT/SE2022/050484 mailed Nov. 14, 2022, 12 pages.

* cited by examiner

DETERMINATION OF HAPTOGLOBIN QUANTITY IN MILK

CROSS-REFERENCE TO RELATED APPLICATIONS

This application is the U.S. national phase of International Application No. PCT/SE2022/050484 filed May 18, 2022 which designated the U.S. and claims priority to SE 2150655-5 filed May 24, 2021, the entire contents of each of which are hereby incorporated by reference.

FIELD OF THE INVENTION

The present invention relates to determination of haptoglobin in milk. The invention provides a device and method configured to determine a value of haptoglobin quantity in a milk sample.

BACKGROUND OF THE INVENTION

Milk production in animals, especially cows have been optimized severely over the years through efficiency gain and selective breeding. The higher milk yield requires more feed but also healthy cows and good farm management to be maintained. Until now the industry has mainly been focusing on selective breeding and genetic breeding in relation to milk yield. However, increasing focus on disease detection and treatments is starting to be of more interest. Monitoring of parameters in the milk from cows could be of support herefore.

Several diseases may affect the milk yield and health status of the cows such as mastitis acute and chronic, ketosis and metabolic disorders, metritis and other reproductive diseases, stress and lameness. Mastitis is a common disease which is an infection in the mammary gland. The consequences are low milk yield and quality. Treatments are based on antibiotics and can be with limited success. Ketosis is a metabolic disorder, which happens the first months after calving. This is often treated with propylene glycol and feed containing high amount of starch (and other sugar derivatives). Metritis is an infection in the uterine. Such infection takes place in the most sensitive part of the lactation with signs of anorexia, depressed mood, reduced appetite, and feed intake with the short-term result that the lactational milk yield become significantly lower than in no metritis cows. Additional effects on the longer term are "low success rate" on inseminations, increasing the open days, which in return extends that time with low milk yield, before the next calving time. Stress affect the well-being of the cow and can give abortions, low milk yield and low success rate of inseminations. Lameness is often caused by laminitis, claw disease, digital dermatitis, and foot rot. This limits the cows ability to move around and hereby access to feed, water and the general welfare of the cow.

Diseases such as metritis, mastitis, lameness and ketosis can be so severe that the outcome is that the cow is set to be culled. Almost all diseases impact profitability on the farm and animals welfare. Optimal treatments and prevention methods for the above-mentioned diseases is thus, of high importance.

For a long time it has been generally known that early detection of diseases increases the chances of effective treatment. Therefore, there is an incentive to increase on farm monitoring and testing. To do this many systems have been developed. Automatic health and reproduction monitoring are emerging to improve efficiency, labor use and animal welfare in a sustainable way.

The mentioned diseases trigger an early defense response of the innate immune system affecting the expression of several proteins. One of these is haptoglobin. Haptoglobin is positively upregulated as a cause of infections and is generally low in healthy cows why it constitutes a good disease marker as a response to infection and inflammation. Haptoglobin's main biological function is to bind free hemoglobin with high affinity to prevent loss of iron after intravascular hemolysis. Haptoglobin is present 24-48 hours after infection and has been demonstrated to be present in milk. Furthermore, studies show that the amount of haptoglobin can be correlated to clinical disease. Haptoglobin is a general health marker. If haptoglobin is used to differentiate between diseases it must be combined with other biomarkers. Haptoglobin can be used to measure the severity of the disease. Haptoglobin can thus be used as a marker for acute vs chronic mastitis, metritis, lameness, respiratory disease and as a general health marker. Thus, haptoglobin could be a rapid, precise and easy diagnostic tool to evaluate the effect of changes in farm management and as a tool to diagnose and obtain a more precise treatment of diseased dairy cows.

Hence, an easy available measurement system for potential on-site measurement of haptoglobin would be advantageous, and in particular, a reliable system for quantitatively measuring of haptoglobin to determine the present health status of milk-producing animals would be advantageous.

OBJECT OF THE INVENTION

In particular, it may be seen as an object of the present invention to provide an analysing unit, preferably comprised in a milking arrangement, and method for easy and reliable measurement of haptoglobin in milk that solves the above mentioned problems and provides the farmer with a readily available tool for establishing the health conditions of his animals.

SUMMARY OF THE INVENTION

Thus, the above described object and several other objects are intended to be obtained in a first aspect of the invention by providing a milking arrangement comprising a milking machine for milking an animal, wherein the milking arrangement comprises

- an analysing unit configured to determining a value of haptoglobin quantity in a milk sample taken from milk harvest by the milking machine, said analysing unit comprising:
  - a haptoglobin sensor device configured to provide a value of haptoglobin quantity in said milk sample, and
  - a processor wherein said processor being configured, on the basis of a reaction time being the time during which said milk sample has been in contact with the haptoglobin sensor device, to:

- determine when the reaction time exceed a threshold time, if the provided value of haptoglobin quantity is above a haptoglobin threshold, and
  - in confirmative case assign the provided value of haptoglobin quantity to be a determined value of haptoglobin quantity, and
  - in non-confirmative case increase the reaction time to a total reaction time and assign the provided value of haptoglobin quantity to be the determined value of haptoglobin quantity at the point in time where the reaction time exceeds the total reaction time.

The invention is particularly, but not exclusively advantageous for obtaining a trustworthy value of haptoglobin being, at least potentially, more accurately determined, and thus to obtain a measurement of haptoglobin quantity of the milk on the farm.

A second aspect of the invention relates to a method of determining a haptoglobin quantity in a milk sample, the method is preferably carried out by use of milking arrangement according to the first aspect and comprising:

obtaining a milk sample, apply the milk sample to the haptoglobin sensor device and determining the point in time when the milk sample is applied to the haptoglobin sensor device, and determine when the reaction time exceed the threshold time, if the provided value of haptoglobin quantity is above a haptoglobin threshold, and in confirmative case assign the provided value of haptoglobin quantity to be a determined value of haptoglobin quantity, and in non-confirmative case increase the reaction time to a total reaction time and assign the provided value of haptoglobin quantity to be the determined value of haptoglobin quantity at the point in time where the reaction time exceeds the total reaction time.

The first and second aspect of the present invention may each be combined with any of the other aspects. These and other aspects of the invention will be apparent from and elucidated with reference to the embodiments described hereinafter.

BRIEF DESCRIPTION OF THE FIGURES

The present invention and in particular preferred embodiments thereof will now be described in greater details with reference to the accompanying figures. The figures show ways of implementing the invention and are not to be construed as being limiting to other possible embodiments falling within the scope of the attached claim set.

Figure 1:
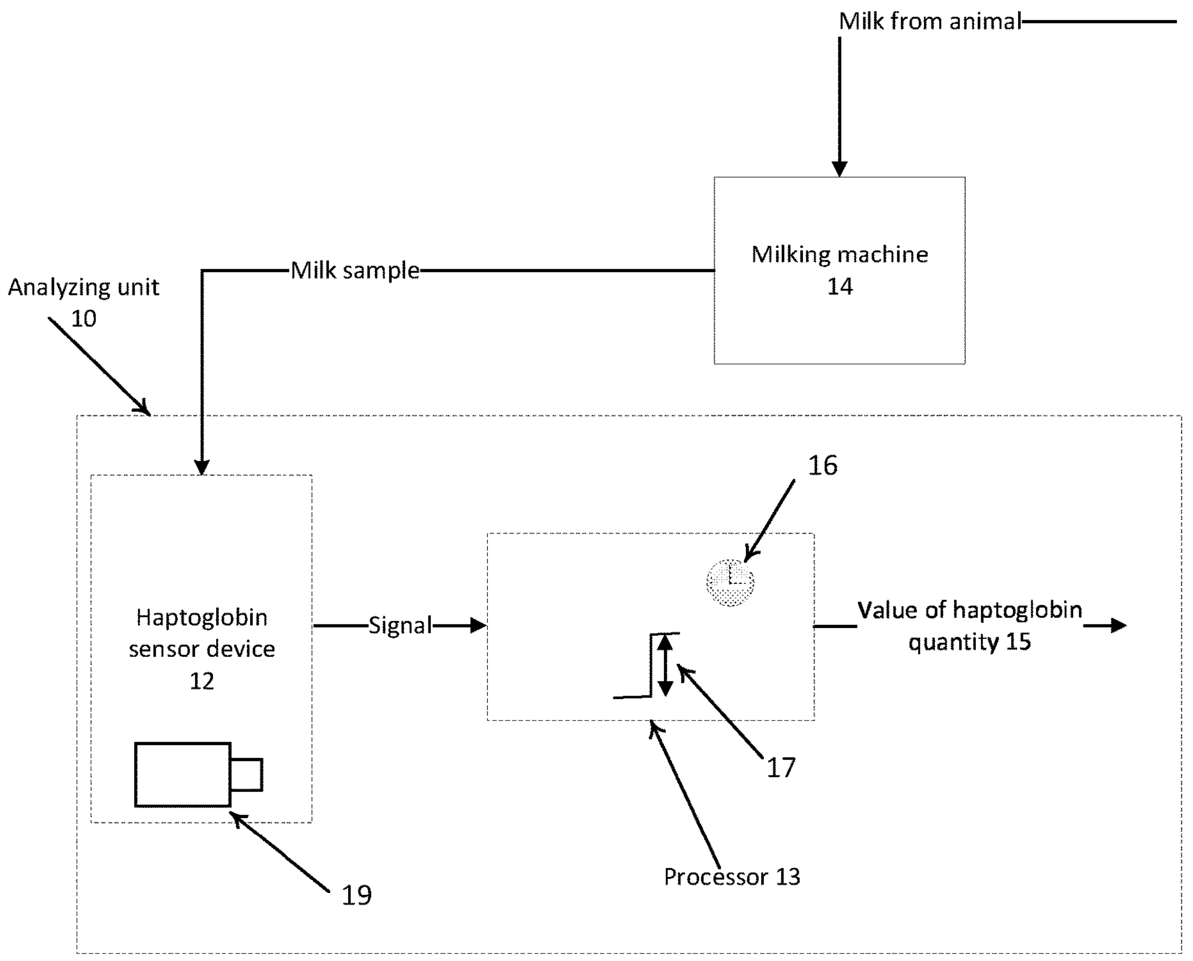
FIG. 1 schematically illustrates a milking arrangement according to a preferred embodiment of the invention.

Reference is made to FIG. 1 schematically illustrating a preferred embodiment of a milking arrangement. Elements of the milking arrangement are illustrated as boxes, and it is to be emphasised that the indicated boxes are not limiting for other ways implementing the milking arrangement. Accordingly, the box illustrating the analysing unit 10 in FIG. 1, does not imply, e.g, that the sensor and processor must be embodied as a single unit, but relates merely to logical connections between the elements. In addition, the milking arrangement may comprise further elements than illustrated.

The milking arrangement comprises a milking machine 14 for milking an animal. The animal is preferably a cow, but the invention may be used for other milk producing animals. "Animal" may be any arbitrary type of domesticated female milk producing and/or meat producing mammal, such as cow, goat, sheep, horse, camel, primate, dairy buffalo, donkey, yak, etc. The milking machine is typically a conventional milking machine which is configured to harvest milk by milking a cow. The milking arrangement is configured to draw a milk sample (not illustrated in FIG. 1) typically of a known volume from milk being milked from the animal and to apply at least a part the milk sample to a haptoglobin sensor device 12.

The milk sample may be mixed with a diluent before being applied to the haptoglobin sensor device.

As illustrated, the milking arrangement comprising an analysing unit 10 configured to determining a value of haptoglobin quantity in a milk sample taken from milk harvest by the milking machine 14. Comprised in the analysing unit 10 is a haptoglobin sensor device 12. This haptoglobin sensor device is configured to provide a value of haptoglobin quantity 15 in said milk sample. By haptoglobin quantity is typically meant either a concentration of haptoglobin or an absolute value of the amount of haptoglobin determined.

As disclosed herein, it has been found that provided values of haptoglobin quantity may change during the time where the milk sample is in contact with haptoglobin sensor device 12. Without being bound by theory, some experiments suggest that if a high accuracy is aimed at, a relatively longer reaction time may be aimed at, whereas if a lesser accuracy can be accepted a shorter reaction time can be aimed at. The reaction time is the time during which the milk sample is in contact with the haptoglobin sensor device 12.

Thus, if no measures are taken and high accuracy is aimed at a dominating factor in measuring capacity will be the longest time needed to obtain the high accuracy. In many instances, it may be concluded that if the haptoglobin quantity provided is high, a high accuracy may not be needed (as the cow is very sick) whereas if the provided haptoglobin value is low, a high accuracy may be needed to reach a conclusion as to the health state of the cow. In the present invention, this has been implemented in some embodiments by using a haptoglobin threshold, where provided values of haptoglobin above the haptoglobin threshold is assigned to be determined values of haptoglobin quantities, which also may be referred to trustworthy values of haptoglobin quantities. Consequently, the reaction time is suggested to be increased if the haptoglobin sensor device provides values of haptoglobin quantities below the threshold.

While such strategies may be implemented by a user manually deciding a reaction time regime, the present invention suggests to apply a processor 13 comprised in the analysing unit to, inter alia, control the provision to determine of the value of haptoglobin quantity.

To this, the processor 13 is in preferred embodiments, configured, on the basis of a reaction time (which is the time during which said milk sample has been in contact with the haptoglobin sensor device), to determine when the reaction time exceed a threshold time. The processor 13 being further configured to determine whether or not the provided value of haptoglobin quantity is above a haptoglobin threshold and in confirmative case assign the provided value of haptoglobin quantity to be a determined value of haptoglobin quantity. And, in non-confirmative case the processor 13 increases the reaction time to a total reaction time and assign the provided value of haptoglobin quantity to be the determined value of haptoglobin quantity at the point in time where the reaction time exceeds the total reaction time.

In a preferred embodiment, the processor 13 is configured to determine the point in time when the milk sample is applied to the haptoglobin sensor device 12, and this point in time is assigned to be the starting point in time for the reaction time. This is typically an initial step and may be embodied as the haptoglobin sensor device 12 being configured to detect that milk is applied. At this time, the processor starts a time-counter typically comprised in the processor itself or in the analysing unit 10.

In preferred embodiments, the processor 13 comprises a time-counter.

On the basis of the time-counter, the processor determines an elapsed reaction time 18 being the reaction time during which said milk sample is in contact with the haptoglobin sensor device 12. It is clear that the processor does not necessarily determines the elapsed reaction time all the time, but may do so at regular time intervals, such as one time every second.

It is often required that the elapsed reaction time must have exceeded a certain threshold time for the haptoglobin sensor device 12 to provide a trustworthy value of haptoglobin quantity. Accordingly, the processor 13 determines if the elapsed reaction time exceeds or is equal to a threshold time 16. The actual value of the threshold time is initially typically determined by a user based on experiments, and such initial threshold time may be the same for all or at least some milk sample. In some preferred embodiments, the threshold time is selected in accordance with an average milking time whereby the haptoglobin value may be provided at the end of the milking operation. However, milk samples may be further timewise apart, as not necessarily all cows are to sampled at every milking, which may provide more time available for the determination of haptoglobin quantity. In some preferred embodiments, the average milking time is about six minutes and the threshold time may be set to be 6 minutes.

If the elapsed reaction time exceeds or is equal to the threshold time 16, the processor effects that the haptoglobin sensor device 12 provides the value of haptoglobin quantity in milk sample. The processor then compares the provided value of haptoglobin quantity with the haptoglobin threshold 17, and if the provided value is above said haptoglobin threshold 17, the processor assigns the provided quantity to be a determined value of the quantity of haptoglobin in said milk sample.

If, on the other hand, the provided value of haptoglobin value is below said haptoglobin threshold, the processor increases the reaction time to a total reaction time. With this increased reaction time, the processor at later point in time evaluates whether the elapsed reaction time exceeds or is equal to the total reaction time and when that happens the processor assigns the provided value of haptoglobin quantity to be the determined value of haptoglobin quantity at the point in time where the reaction time exceeds the total reaction time.

To avoid too long elapsed reaction time, the total reaction time is typically capped by a predefined maximum of total reaction time.

In embodiments involving a dry stick (a dry stick according to the invention will be described below), the haptoglobin sensor device 12, comprising the dry stick, may have an optical device 19 that is configured to optically read a test signal at the test line 24 of the dry stick 20. As this test signal is correlated with the value of haptoglobin quantity, the test signal can be translated into a value of haptoglobin, e.g. by relating an actual test signal to signals obtained on the basis of milk samples with known amounts of haptoglobin as will be disclosed below.

The determination of the value of haptoglobin quantity is in preferred embodiments carried out by the processor 13 receiving the test signal and optionally a control signal. The processor 13 is configured to determine the provided value of haptoglobin quantity based on the received test signal. The processor 13, in general, has software allowing it to translate the test signal into a provided value of haptoglobin which software implements a correlation between test signal and value of haptoglobin quantity or performs a look-up in a database storing corresponding test signals and haptoglobin quantities. Examples on these are provided below.

In situations where the dry stick has a control line, the optical device may be configured to optically read also a control signal at the control line.

In particular preferred embodiments, the haptoglobin sensor devices utilizes a dry stick. Preferably, the dry stick is a competitive lateral flow stick configured to measure haptoglobin in a milk sample, said dry stick comprises:

- a base pad capable of allowing lateral flow of fluid there through;
  - comprising a labelled-control conjugate and a labelled-conjugate diffusibly arranged herein, wherein said labelled-conjugate binds haptoglobin, and wherein a complex is formed between said labelled-conjugate and said haptoglobin when said dry stick is in use;

wherein said base pad further comprises

- a test line comprising immobilised target analyte, wherein said immobilised target analyte binds to said labelled-conjugate when not in said complex; and
- a control line, which is spaced from said test line, and which comprises control analyte capable of binding to said labelled-control conjugate.

It is noted, that the control line is an optional feature. However, the below description has been made with reference to dry stick comprising both the control line and the test line.

By competitive lateral flow stick is to be understood that the dry stick is capable of allowing a lateral flow of liquid from one end of the dry stick to the other end of the dry stick as commonly known to the skilled person. By competitive is to be understood that the target analyte at the test line competes with haptoglobin in the sample for binding to the labelled-conjugate.

A dry stick as herein described may be implemented in a milking arrangement, potentially via a cassette, as described in e.g. WO 2020/251457.

Base Pad

The dry stick comprises a base pad for allowing a lateral flow to take place. In its most simple form the base pad only comprises one module. However, the base pad may also comprise more modules, which can be of different materials depending on the specific purpose of the module. In an embodiment, said base pad comprises at least two modules. Hereby is to be understood that the base pad may comprise two or more modules.

In a further embodiment, the base pad comprises two modules being a membrane and a reagent pad. In a further embodiment, said membrane or at least a part hereof is downstream of said reagent pad.

In a further embodiment, the base pad comprises three modules being a membrane, a sample pad and a conjugate pad. In a further embodiment, said membrane or at least a part hereof is downstream of said conjugate pad and said conjugate pad or at least a part hereof is downstream of said sample pad.

In a further embodiment, a module is a reagent pad capable of receiving said milk sample. Hence, the base pad would comprise a module being a reagent pad. In an even further embodiment, said reagent pad comprises at least two modules being a sample pad and conjugate pad. In a further embodiment, the sample pad and the conjugate pad are partly overlapping. In one embodiment, the base pad comprises at least two modules, wherein one of said at least two modules is a sample pad capable of receiving said milk sample. If the reagent pad is one module, the sample pad and conjugate pad will be contained in this module and the milk sample will be received in the reagent pad.

In the present context, “reagent pad” relates to one or more pads comprising the labelled-control conjugate and the labelled-conjugate, which are both diffusible arranged in the reagent pad. The milk sample would also be applied to the reagent pad. In one embodiment, the reagent pad comprises a sample pad and a conjugate pad.

The material used for the reagent pad may be selected from the group of a nitrocellulose membrane, a cellulose, a polymer such as nylon, a polyvinylidene fluoride or latex, glass fibres, woven fibres, non-woven fibres and a chromatographic gel membrane.

In the present context, “sample pad” relates to a pad in the dry stick where the milk sample is applied to the dry stick and which provides a fast adsorption of the liquid sample and a fast and consistent release of the sample to the conjugate pad. The purpose of the sample pad is to collect sample. In some embodiments, it can be designed to withhold not wanted molecules present in the sample for these not to interfere with the functioning of the dry stick such as removing red blood cells, fat aggregates and large particles. The sample pad may be treated with a surfactant to release surface tension and quickly soak in the sample.

The material used for the sample pad may be selected from the group of a nitrocellulose membrane, a cellulose, a polymer such as nylon, a polyvinylidene fluoride or latex, glass fibres, woven fibres, non-woven fibres and a chromatographic gel membrane.

In the present context, “conjugate pad” relates to one or more pads comprising the labelled-control conjugate and the labelled-conjugate, which are both diffusible arranged in the conjugate pad.

The material used for the conjugate pad may be selected from the group of a nitrocellulose membrane, a cellulose, a polymer such as nylon, a polyvinylidene fluoride or latex, glass fibres, woven fibres, non-woven fibres and a chromatographic gel membrane.

In the present context, “diffusibly arranged herein” relates to the labelled-control conjugate and the labelled-conjugate being present in the base pad in a manner, which allows the labelled-control conjugate and the labelled-conjugate to be immobilised when the dry stick is in dry state and mobile when in moistened state i.e. when in use. Accordingly, the labelled-conjugate and the labelled-control conjugate will be maintained in the base pad e.g. in the reagent pad or conjugate pad when the dry stick is not used. When sample is added to the dry stick, the induced flow will transfer the labelled-control conjugate and the labelled-conjugate along the flow.

In a further embodiment, said base pad comprises a membrane; said membrane comprising said test line and said control line. In a further embodiment, said membrane is a nitrocellulose membrane. In one embodiment, one of the modules of the base pad is a membrane such as a nitrocellulose membrane. The nitrocellulose membrane has a porous structure, which makes it suitable for migration of liquid through capillary action. The membrane comprises two lines—a test line and a control line. Flow rates along the dry stick may be controlled by the characteristics of the membrane.

In a still further embodiment, said dry stick further comprises an absorbent pad. In the present context, the term “absorbent pad” refers to a material, which has the purpose of absorbing any liquid in excess when it has migrated through the base pad. Furthermore, backflow is prevented, which could cause incorrect results. Accordingly, the absorbent pad is arranged downstream of the test line and control line.

The material for the absorbent pad can be any material having great absorption characteristics such as a cellulose based material.

In an even further embodiment, said dry stick further comprises a backing card. In the present context, the term “backing card” refers to a material, which has no influence on the migration or on the reaction of the liquid sample or on reagent(s) or the agents capable of increasing the rate of the reaction. The backing card provides a stabilising basis for the dry stick and provides sufficient strength to maintain the desired physical shape and has substantially no interference with the production of a detectable signal. Thus, the backing card supports and stabilises at least a part of the base pad and potentially at least a part of the absorbent pad. In an embodiment of the present invention, the material for the backing card is selected from the group of polystyrene, vinyl and adhesive.

In a further embodiment, said dry stick further comprises a cover tape. In an even further embodiment, said cover tape covers at least said conjugated pad. In the present context, the term “cover tape” refers to a material, which has the purpose of making contact between the different membranes and/or pads. It has no chemical function but serves solely to apply pressure and contact between the different modules. The material could be any clear tape, where the adhesive does not have any influence flow of the dry stick.

In yet an embodiment of the present invention, the modules of the dry stick are in contact with one another by substantially fully overlapping, by partially overlapping or by laying adjacent to one another. In a further embodiment, said at least two modules partly overlaps. In an embodiment of the present invention the modules are overlapping by at least 5%, such as at least 10%, e.g. at least 25%, such as at least 50%, e.g. at least 75%, such as at least 80%, e.g. at least 90%, such as at least 95%. In the present context the term “substantially fully overlapping” relates to two separate modules being placed on top of one another. In the present context the term “partially overlapping” relates to two separate modules being overlapping with only part of the modules. A partial overlap of 100% relates to a full overlap and a deviation of 5% from the 100% full overlap relates to a substantially full overlap.

In an embodiment of the present invention the modules are laying adjacent to one another. This means that the pads are placed in contact with each other (touching each other). An overlap of 0% (but in contact) relates to the term “laying adjacent”, furthermore, an overlap of less than 5% may be considered being within the term of “laying adjacent”, such as an overlap of at the most 4%, e.g. an overlap of the most 3%, such as an overlap of the most 2% or e.g. an overlap of the most 1%.

In a preferred embodiment, the dry stick comprises a backing card and a base pad having three modules being a sample pad, a conjugate pad and a membrane having a control line downstream of the test line. The sample pad partially overlaps with the conjugate pad, which partially overlaps with the membrane. The dry stick furthermore comprises an absorbent pad downstream of the membrane and partially overlapping herewith.

In a further preferred embodiment, the dry stick comprises a backing card and a base pad having two modules being a reagent pad and a membrane having a control line downstream of the test line. The reagent pad partially overlaps with the membrane. The dry stick furthermore comprises an absorbent pad downstream of the membrane and partially overlapping herewith.

Test Line and Control Line

The test line comprises a target analyte capable of binding to the labelled-conjugate, when not bound to haptoglobin. The control line comprises a control analyte capable of binding to the labelled-control conjugate. Accordingly, the control line is independent of the test line. In one embodiment, said control line is downstream of said test line. This is highly advantageous as it follows from the independency that the control line is to ensure that the stick is functioning and thus, the result obtained in the test line valid. When arranging the control line downstream of the test line, the functioning is tested after the test line and thus, it follows that the flow in the dry stick is correct at least until the control line is reached.

The wording “line” refers to the area where the target analyte and control analyte, respectively, are immobilized on the dry stick. This is often in the shape of a line, however, it may also be formed in a different geometrical pattern as long as the read-out of the binding to the target analyte and control analyte is feasible.

In the present context, “control analyte” is to be understood as the compound immobilized at the control line, which is capable of binding to the labelled-control conjugate. The control analyte is an immobilised control analyte. Hereby, is to be understood that the control analyte will remain at the control line even when said dry stick is in use.

The control analyte may be selected from the group of monoclonal antibodies, polyclonal antibodies, chimeric antibodies, nanobodies, aptamers and antibody mimicking proteins. In an even further embodiment, said control analyte is a third antibody.

In one embodiment, the concentration of the control analyte at the control line is 0.01-2 mg/ml, such as 0.02-1 mg/ml, like 0.05-0.5 mg/ml, such as around 0.2 mg/ml.

In the present context, “target analyte” is to be understood as the compound immobilized at the test line. The target analyte is capable of binding to the labelled-conjugate but not when the conjugate is in complex with haptoglobin. Accordingly, the target analyte may be haptoglobin or a part hereof as long as this part is able to bind to the labelled-conjugate in a competitive manner with the haptoglobin protein present in the milk sample. Alternatively, the target analyte may be a fusion protein comprising at least the part of haptoglobin binding to the labelled-conjugate. As an example, at least the part of haptoglobin binding to the labelled-conjugate or haptoglobin as such could be fused to bovine serum albumin (BSA). Alternatively, at least the part of haptoglobin may be biotinylated for immobilisation purposes.

The target analyte is an immobilised target analyte. Hereby, is to be understood that the target analyte will remain at the test line even when said dry stick is in use.

In one embodiment, the concentration of the target analyte at the test line is 0.01-2 mg/ml, such as 0.02-1 mg/ml, like 0.05-0.5 mg/ml, such as around 0.1 mg/ml.

In the present context, “complex” relates to a molecular entity formed by association between the labelled-conjugate in the base pad and the haptoglobin potentially present in the milk sample, which will form when the dry stick is in use i.e. when a sample is added to the dry stick and said sample comprises haptoglobin.

In one embodiment, the width of the control line and/or test line is 0.5-5 mm, such as 1-3 mm, like around 2 mm and the distance between the lines would be at least 0.5 mm, such as at least 1 mm in order to allow for sufficient distance between the lines. This would also allow for measurement of a background between the test line and control line to enable a more reliable measurement of the output of the test line and control line.

In a further embodiment, the target analyte and/or control analyte may be immobilized on the test line and/or control line, respectively by using blocking compounds such as polyvinylpyrrolidone (PVP), polyethylene glycol (PEG), bovine serum albumin (BSA) and salts like NaCl and KCl, to help bind the control analyte and/or target analyte to the base pad.

In addition, or alternatively, the target analyte and/or control analyte may be accompanied by pH-regulating agents such as Tris buffers, phosphate buffers and glycine buffers, for stabilising the pH and hence the secondary structure of the protein.

In a still further embodiment, surfactants may be included like Tween-20, Triton x-10, Plurionic, Tegretiol 20.

Milk Sample

In the present context, “milk sample” is to be understood as a milk sample obtained directly from the animal after milking, where the sample has not yet been processed to consumer milk.

The animal is preferably a cow, but the invention may be used for other milk producing animals. “Animal” may be any arbitrary type of domesticated female milk producing and/or meat producing mammal, such as cow, goat, sheep, horse, camel, primate, dairy buffalo, donkey, yak, etc.

Advantageously, the dry stick may comprise a surfactant for the milk sample to provide optimal mix, release and line morphology when running the milk samples. In one embodiment, said base pad further comprises a surfactant. In a further embodiment said sample pad comprises said surfactant. In an even further embodiment, said surfactant is comprised in said reagent pad. In particular, the use of a surfactant in connection with the milk sample is beneficial with respect to the measurement of haptoglobin as the viscosity of the milk is usually increased for animals suffering from a disease.

In one embodiment, said surfactant is Pluronic F68, Pluronic F127, Surfactant 10G, Synperonic F108, Tergitol, Tween-20 and/or Triton X-100.

In a further embodiment, said surfactant is in a concentration in the range of 0.1-5 w/w %, such as 0.5-4 w/w %, like 1-3 w/w %, such as around 2 w/w %.

In an even further embodiment, said base pad comprises a pH-regulating agent. In a still further embodiment, said pH-regulating agent is a phosphate buffer, a borate buffer, a citric acid buffer and/or a Tris buffer. The pH-regulating agent ensures that the pH is maintained in the milk sample around a pH resembling that of the milk sample. In one embodiment, said milk sample has a pH in the range of 6-9. In a further embodiment, the milk sample has a pH in the range of 6.4-8.5. Hereby, the confirmation of the proteins in the milk sample will maintain as naturally occurring and allow for optimal binding of haptoglobin to the labelled-conjugate and/or optimal binding of the target analyte to the labelled-conjugate. Accordingly, pH is maintained optimal during the use of the dry stick.

In addition, further components may be added to the base pad and in particular to the conjugate pad in order to obtain a better release of the conjugate and the control-conjugate and validity of the results obtained when using the dry stick. Such compounds may be Sucrose and Trehalose. In one embodiment, these compounds are added in a concentration of 0.1-5 w/w %, such as 0.5-4 w/w %, like 1-3 w/w %, such as around 2 w/w % each.

Alternative or additionally to adding a surfactant to the base pad, sample pad and/or reagent pad, the milk sample may be mixed with a surfactant before providing it to the dry stick. In a further embodiment, said milk sample is mixed with a diluent comprising a surfactant, prior to applying said milk sample to said dry stick. In an even further embodiment, said surfactant is present in the diluent in a concentration of 0.1-4 w/w %, such as 0.5-2 w/w %, like around 1 w/w %.

In a still further embodiment, said surfactant is one or more surfactants selected from the following group: Pluronic F68, Pluronic F127, Surfactant 10G, Synperonic F108, Tergitol, Tween-20 and/or Triton X-100. In a still further embodiment, said surfactant is Tween-20.

Advantageously, the addition of a diluent increases the flowrate and mixing properties of the sample.

The diluent may beside water and surfactant comprise a pH regulating agent e.g. Tris-(hydroxymethyl)-methylamine), stabilizers e.g. sodium chloride, blocking agents e.g. PVP 40 and conservation agents e.g. ProClin 300. This would increase the reproducibility e.g. by blocking non-specific binding. Other pH regulating agents, stabilizers, blocking agents and conservation agents as commonly known to the skilled person may also be used.

The pH-regulating agent may be provided with the diluent. The concentration of the pH-regulating agent in the diluent is preferably in the range of 0.01-0.99 w/w %, such as 0.1-0.9 w/w %, like 0.25-0.75 w/w %, such as 0.35-0.65 w/w %, like around 0.5 w/w %.

Conjugate

In the present context, “labelled-conjugate” relates to the chemical substance that binds to haptoglobin in the milk or to the target analyte on the test line. The labelled-conjugate is a conjugate labelled with a label. Labelled-conjugate may relate to different labelled-conjugates such as two or more labelled-conjugates, such as three or more labelled-conjugates. However, in one embodiment, only one labelled-conjugate is present in the dry stick. The labelled conjugate may comprise a conjugate being selected from the group of monoclonal antibodies, polyclonal antibodies, chimeric antibodies, nanobodies, aptamers and antibody mimicking proteins. In one embodiment, said labelled-conjugate is a labelled first antibody.

In one embodiment, the concentration of the labelled-conjugate is 0.5-20 g/ml, such as 1-15 μg/ml, like 2-12 μg/ml, such as 3-10 μg/ml, like 4-7 μg/ml, such as around 5 μg/ml.

In the present context, “labelled-control conjugate” relates to the chemical substance that binds to the control analyte at the control line. The labelled-control conjugate is a control conjugate labelled with a label. Labelled-control conjugate may relate to different labelled-control conjugates such as two or more labelled-control conjugates, such as three or more labelled-control conjugates. However, in one embodiment, only one labelled-control conjugate is present in the dry stick. The labelled-control conjugate may comprise a control conjugate being selected from the group of monoclonal antibodies, polyclonal antibodies, chimeric antibodies, nanobodies, aptamers and antibody mimicking proteins. In a further embodiment, said labelled-control conjugate is a labelled second antibody.

The concentration of the control analyte in the control line is 1-30 μg/ml, such as 2-25 μg/ml, like 4-20 μg/ml, such as 5-15 μg/ml, like 7-12 μg/ml, such as around μg/ml.

The labelled-control conjugate and the labelled-conjugate may be added to the conjugate pad by soaking, dip coating and spraying as commonly known to the skilled person in the art. This may be performed either manually or automatically.

The labelled-control conjugate and the labelled-conjugate are labelled with a label in order to be identified at the control line and the test line. The label would depend on the measuring system for the measurement of the labelled-control conjugate and labelled-conjugate present at the control line and test line, respectively. Thus, the labels may be chosen by the skilled person according to the wishes of the read-out. The label may be selected from the group of colloidal gold particles, latex particles, cellulose nanobeads, paramagnetic particles, radioactive particles and fluorescent particles as well as enzymes. In one embodiment, said labelled-control conjugate and/or said labelled-conjugate is labelled with colloidal gold particles.

Standardly, the three major groups of labels are: gold nanoparticles, latex particles and fluorescent particles.

The gold particles are gold particles often with a diameter around 40 nm. The particles are often called colloidal gold particles, since they are in a stable dispersion and require a specific pH and additives to the dispersion. These particles have a reddish/purple color. The small size gives a quick release and less issues with aggregation. However, sensitivity is often lower, since the color formation is lower per conjugate and thereby requires more conjugates. This is due to the smaller size and thereby the less reflection surface. The conjugation of conjugates to the gold particles is done passively, meaning it utilizes a combination of the electrostatic surface of the colloidal gold and hydrophobic interactions to bind the protein to the gold particles. As an example, it may be performed by mixing the conjugate and gold particles at a specified pH, adding excess bovine serum albumine and removing all unbound conjugate by centrifugation.

Latex particles are microspheres made of polyesters. These have a size of about 200-400 nm in diameter. They can be made in a variety of colors such as blue, green, purple and red. The particles are larger meaning less conjugate is required to create a visual color than for gold particles. Thus, less conjugate would be needed per dry stick, which could result in more variation and less flexibility. The bigger size may cause issues in relation to release and aggregation. The conjugate and label is normally covalently conjugated.

Fluorescent particles give high sensitivity and detect analytes at very low concentrations (pg/mL). A disadvantage is that it requires a specific light source for reading of the result but the advantages are improved sensitivity. There are multiple different types of fluorescent labels, such as organic dyes, metal-ligand complexes, fluorescent proteins, semiconductor quantum dots, lanthanide complexes, dye-doped polymer nanoparticles, fluorescent silica nanoparticles, xanthene dyes and cyanine dyes. In addition, fluorescence proteins can also be utilized. These different types of fluorescent dyes have different absorbance and emission wavelengths why it may be used for multiplexing.

The labels may be conjugated to the conjugate and/or control conjugate either passively or covalently.

EXAMPLES

Example 1—Dry Stick for Haptoglobin Measurement

In one embodiment, the dry stick 20 may be designed as disclosed in FIG. 2A-B, where A shows a side view of the embodiment and B shows a top view. The dry stick 20 comprises a backing card 33 on which a sample pad 35, a conjugate pad 39, a membrane 41 and an absorbent pad 43 are arranged. Each of these different modules are partially overlapping to provide a smooth flow. The milk sample is added to the sample pad 35 and mixes with the conjugate (i.e. labelled-control conjugate and labelled-conjugate) in the conjugate pad 39 due to the downstream lateral flow 59 in the dry stick 20. Haptoglobin in the milk sample will bind to the conjugate to form a complex. Downstream of the conjugate pad 39 the membrane 41 comprises a test line 24 and a control line 25, which will bind to conjugate and control conjugate, respectively, from the conjugate pad 39. At the end of the run, the milk sample will be absorbed by the absorbent pad 43 at the end of the dry stick 20. Hereby, backflow is avoided along with contamination of the result. In addition, the dry stick will often hold a cover tape (not shown) to create pressure on all contact spots between the different materials and to ensure sufficient flow.

FIG. 3A-C show one embodiment of a dry stick prior according to the invention. FIG. 3A shows one embodiment of a dry stick prior to testing a milk sample. In this embodiment, the conjugate pad and the sample pad are shown as one module (i.e. reaction pad 38). The milk sample is introduced to the reaction pad 38, which comprises labelled-control conjugate 51 as well as labelled-conjugate 53. At the test line 24, target analyte 55 is present, while the control line 25 comprises control analyte 57.

If no haptoglobin is present in the milk sample, the labelled-conjugate 53 will bind to the target analyte 55 as demonstrated in FIG. 3B. In addition, the labelled-control conjugate 51 will bind to the control analyte 57. Hereby, a negative result is obtained being labelled both in the control line as well as the test line. In case of a positive result i.e. that haptoglobin 58 is present (shown in FIG. 3C) the haptoglobin will form a complex with the labelled-conjugate 53 prior to arriving at the test line 24 preventing the labelled-conjugate 53 from binding to the target analyte 55 at the test line 24. Nevertheless, the labelled-control conjugate will bind to the control analyte 57 at the control line 25. Thus, the dry stick will only be labelled at the control line 25. Depending on the concentration of haptoglobin in the milk, the labelled-conjugate 53 binds to the test line 24 correlating negatively (competitive) with the concentration haptoglobin. Accordingly, the intensity of the labelling at the test line 24 will vary depending on the amount of haptoglobin present in the milk sample.

The labelling at the control line 25 is independent of the amount of haptoglobin present in the milk sample and is a control of the lateral flow as such and the release of the conjugates from the conjugate pad. If the lateral flow has run satisfactorily and the conjugates been released as should be from the conjugate pad, a labelling will appear at the control line 25. If no labelling is registered at the control line 25, the result obtained by the dry stick cannot be trusted. It is thus advantageous for the control line to be present downstream of the test line for the results at the test line to be considered valid.

According to preferred embodiments of the invention, the milk sample is provided to the dry stick in a defined amount. This would be needed if the exact value of haptoglobin quantity present in the milk sample is to be determined.

The control line may serve as a quality assurance indicating that the function of the dry stick is desired in the sense that if a control signal is produced, the dry stick is said to functions as desired.

However, it has been found that inter alia aging of a dry stick may influence the colour intensity produced by the test line and, if implemented, also the colour intensity of the control line. Aging refers to the storage time of the dry stick and under which condition the dry stick has been stored. The colouring of the test line and control line is the result of the binding of the labelled-conjugate and labelled-control conjugate to the lines and the colour intensity is correlated with the amount of labelled conjugate and labelled-control conjugate which binds to the control line and test line respectively. Without being bound by theory, it is suggested that less labelled conjugate and less labelled-control conjugate are released with increasing time. In attempt to at least mitigate such aging effects, the invention suggests to use a ratio R between test signal and control signal as: R=test signal/(test signal+control signal). This ratio R is in such cases correlated with the value of haptoglobin quantity and is found to be essentially independent on the amounts of labelled conjugate and labelled-control conjugate released from the conjugate pad by the milk applied to dry stick.

Reading of a dry stick may be implemented as described in e.g. WO2020/251460.

In preferred embodiments wherein the optical device 19 comprises a CCD-chip or a camera, such as a CCD camera, configured to optically read a colour intensity of the test line and optionally the control line. Such CCD-chip or camera provides a pixelated image of the test line and, optionally, the control line where each pixel represents a colour and its intensity. The test signal may be obtained in numerous manner, readily available to the skilled person, and may involve a spatial averaging or summation of the pixel values belonging the test and optionally the control line.

In accordance to this, the processor 13 may be configured to determine the test signal and optionally the control signal on the basis of a colour intensity of the test line and optionally across the control line.

Once the test signal and optionally the control signal has/have been provided the provided value of the haptoglobin quantity may be determined. The test signal is correlated with the value of haptoglobin quantity and a number of approaches are available to determine the value of haptoglobin quantity. A common denominator for some of the approaches is that a number of controlled experiments are carried out during which known and different amounts of haptoglobin are added to a plurality of known amounts of milk samples. Thereby, the amount of haptoglobin quantity is known for a plurality of milk samples. During these experiments, the haptoglobin sensor device is used to provide a value of haptoglobin in the milk samples. The thereby provided test signals are recorded and stored in a first database together with added amounts haptoglobin for each sample. Each such set of data may symbolically be written as [Test signal; $HP_{added}$] wherein HP refers to haptoglobin amount. If the control line is taken into account, the control signal may also be stored.

Upon providing values of haptoglobin quantity for milk sample with unknown value of haptoglobin quantity, the milk sample may be exposed to the haptoglobin sensor device providing a test signal. The provided value of haptoglobin quantity may then be derived through a database look-up in e.g. the database disclosed above storing corresponding values of test signal and optionally control signal and haptoglobin quantity. The actual value of haptoglobin quantity may be found by interpolation or extrapolation based on the data stored in the database.

Instead of using database, the data obtained by the experiments may be used in a regression analysis to provide e.g. a functional relationship between the data.

As an alternative to a database look-up, the provided value of haptoglobin quantity can be based on an algebraic relationship between the test signal and optionally the control signal and haptoglobin quantity. Such an algebraic relationship may be provided by regression analysis based on a plurality of experiments as disclosed above in relation to providing a database for database look-up.

A suitable dry stick 20 useable in connection with the present invention has found to be a dry stick which has a base pad capable of allowing lateral flow of fluid there through. In addition, the dry stick has a labelled-control conjugate and a labelled-conjugate diffusibly arranged herein. The labelled-conjugate binds haptoglobin, and a complex may form between the labelled-conjugate and said haptoglobin when said dry stick is in use, that is after milk sample has been applied to the dry stick.

The base pad further has a test line with immobilised target analyte, wherein the immobilised target analyte binds to said labelled-conjugate when not in the complex. The base pad may also have a control line, which is spaced from said test line, and which has specific binding means capable of binding to said labelled-control conjugate.

The progress over time of the provided value of haptoglobin quantity may be influenced by inter alia the environmental conditions to which the milk sample is exposed when in contact with the haptoglobin sensor 12 during the reaction time. If such influences are found to play an important role in the determination of the value of haptoglobin quantity, the milking arrangement may be equipped with an incubator 30 for incubating the milk sample which has been applied to the haptoglobin sensor device 12. Such an incubator may typically comprise a void inside which the temperature and/or the humidity is/are controlled to be within selected ranges. In embodiments involving a dry stick, the dry stick is arranged in the incubator after milk is applied to it. The dry stick is then incubated for the threshold time 16 after which the above disclosed procedure is carried out pertaining to determine a value of haptoglobin quantity. It has been found that use of an incubator may reduce the reaction time in the sense that a trustworthy haptoglobin determination may be provided at a relatively shorter time when an incubator is used. This may turn into that the threshold time may be set relatively shorter than if no incubator is used.

When haptoglobin sensor device 12 comprises an optical device to read a test signal, the optical device may advantageously be arranged to read the dry stick while inside the incubator 30 to eliminate the necessity to remove the dry stick from the incubator.

Many haptoglobin sensor devices and in particular those using dry stick provides an value of haptoglobin quantity that increases with increasing reaction time. It is noted, that the provided value of haptoglobin quantity often goes asymptotic toward a steady state. The haptoglobin threshold is typically determined manually as a value above which there is found no need to further increase the accuracy of the determination the value of the haptoglobin quantity in the milk sample. The haptoglobin threshold may be a value of haptoglobin quantity which reflect a cow being very sick. The haptoglobin threshold is typically also set at a level below which a further reaction time is needed to reach a decisive result as to the value of haptoglobin quantity in a milk sample. Some non-limiting examples of haptoglobin threshold are a haptoglobin threshold larger than 2.0 μg haptoglobin per ml milk, preferably larger than 3.0 μg haptoglobin per ml milk, such as larger than 4.0 μg haptoglobin per ml milk and smaller than 20.0 μg haptoglobin per ml milk.

While the haptoglobin threshold may be used as a decisive parameter, the threshold time may also play an important role due to the timewise progression of the provided value of haptoglobin quantity by the haptoglobin sensor device 12. The value of the threshold time may typically be selected so that a value provided by the haptoglobin sensor device expectedly can be given some merit or at least that a value can be provided. Non-limiting examples of the threshold time initially set are larger than 3.0 minutes, preferably larger than 4.0 minutes, such as larger than 5.0 minutes, preferably larger than 6.0 minutes, and smaller than 10 minutes and less than the maximum of total reaction time. "Initial set" is used to refer to the situation where the reaction time is increased, so that initial refers to the value before being increased.

Non-limiting experiments carried out with a haptoglobin sensor using dry stick suggest that the value of haptoglobin quantity goes asymptotic towards a steady state at which point the benefit of higher accuracy is no longer balanced by the prolonged reaction time. Based on this, preferred embodiments of the invention makes use of total reaction time which when reached terminates further increase of reaction time. At that time, the provided value of haptoglobin is assigned to be a determined value of haptoglobin quantity. Non-limiting examples of the total reaction time are less than 15.0 minutes, such as less than 14.0 minutes, preferably less than 13.0 minutes, such as less than 12.0 minutes, preferably less than 11.0 minutes, such as less than 10.0 minutes, preferably less than 10.0 minutes. It is noted that the total reaction time is larger than the initial threshold time.

A milking arrangement according to the invention may advantageously be implemented in e.g. a herd management system where each animal, such as each cow, is uniquely identifiable e.g. by a tag containing an identification number unique for each animal. To this, the analysing unit is configured to digitally receive an identifier uniquely identifying a particular animal from which the milk sample is taken. This could for instance be provided by the milking arrangement comprising a reader configured to optical read a number provided e.g. on an ear tag placed on the animal or to electronically read e.g. an RIF tag arranged on or in the animal. When a value haptoglobin quantity is determined, the processor is configured to digitally link the identifier and the determined value haptoglobin quantity for the milk sample taken from said particular animal. The determined value of haptoglobin quantity together with the identifier are typically stored as a record in a database for later access. The processor 13 may also be configured to digitally output the linked identifier and determined value of haptoglobin quantity. This could for instance be output optionally together with an interpretation of the determined value of haptoglobin quantity to a farmer allowing the farmer to e.g. contact a veterinarian.

As briefly disclosed above, the analysing unit 13 may in some embodiments comprise a time-counter configured to count the elapsed reaction time. The processor is in such embodiments configured to start the time-counter when it determines the point in time when the milk sample is applied to the haptoglobin sensor device 12.

The processor 13 may determine the point in time when the milk sample is applied to the haptoglobin sensor device 12 on the basis of a user input. This may be implemented by a user pressing a button when the milk sample is applied to the haptoglobin sensor, where the press on the button generates a signal to the processor indicative on that milk has been applied to the haptoglobin sensor device 12. In many instances, there is a desire to carry out the haptoglobin determinations in an automated fashion and in such cases a digital input is automatically provided to the processor 13 in response to milk being applied to the haptoglobin sensor device 12. Such input may be generated in a number of ways, including for instance that a device used for applying milk to the sensor device 12 generates a signal upon applying, the sensor device 12 generates a signal in response to having received milk or a device detects that milk is applied to the sensor device 12.

In modern handling of herds, milking is carried automated or at least semi-automated, and to allow for such automation the milking arrangement has a milking machine 14 configured to milk an animal. Such a milking machine 14 harvest milk from the animal in larger amounts that what is to be applied to the haptoglobin sensor device 12 and there is therefore a need to extract from the harvest milk a smaller amount of milk. To this, the milking arrangement has a sampling device fluidicly connected to milking device to sample a milk sample and apply at least a fraction of the milk sample to said haptoglobin sensor device 12.

While the above disclosure has been focused on a hardware implementation, the invention also relates to a method of determining a haptoglobin quantity in a milk sample. The method, also disclosed in FIG. 4 as flowchart, is typically carried out by use of a milking arrangement as otherwise disclosed herein.

Figure 4:
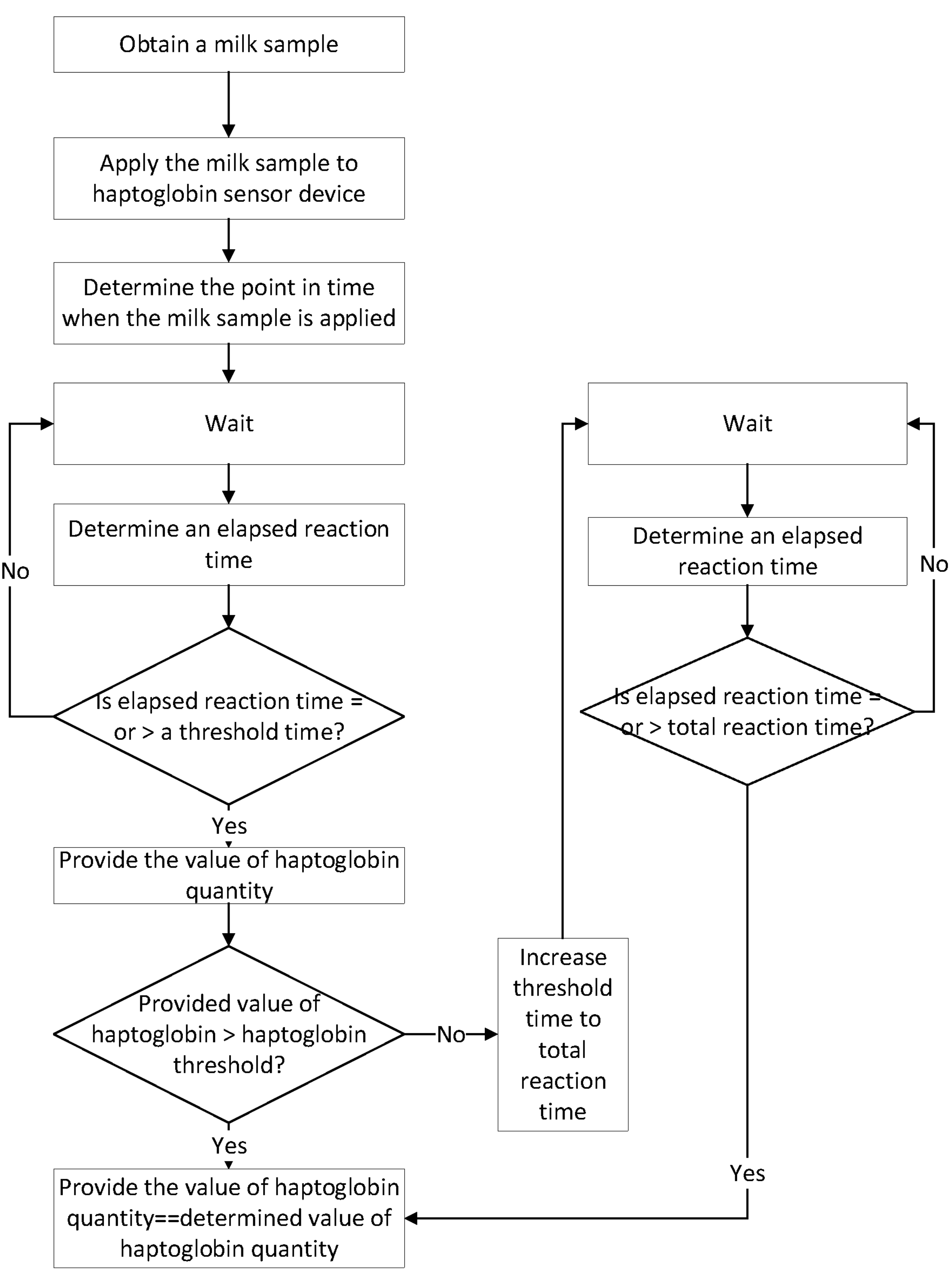
FIG. 4 is a flowchart schematically illustrating steps involved in a preferred embodiment of the invention, FIG. 5 schematically illustrates a milking arrangement according to another preferred embodiment.

As disclosed in FIG. 4, method involves the following step:

- obtaining a milk sample, apply the milk sample to the haptoglobin sensor device 12 and determining the point in time when the milk sample is applied to the haptoglobin sensor device 12, and
- determine when the reaction time exceed the threshold time, if the provided value of haptoglobin quantity is above a haptoglobin threshold, and
  - in confirmative case assign the provided value of haptoglobin quantity to be a determined value of haptoglobin quantity, and
  - in non-confirmative case increase the reaction time to a total reaction time and assign the provided value of haptoglobin quantity to be determined value of haptoglobin quantity at the point in time where the reaction time exceeds the total reaction time.

FIG. 4 also illustrates that the method comprises a waiting period between the step of determining the point in time when the milk sample is applied to the haptoglobin sensor device 12 and the step of determining an elapsed reaction time. This waiting period is included to control frequency at which it is checked whether the elapsed reaction time exceeds or is equal to the threshold time. The length of the waiting period is selected in accordance with the threshold time so that the length of the waiting period preferably is equal to or smaller than the initial threshold time.

Figure 5:
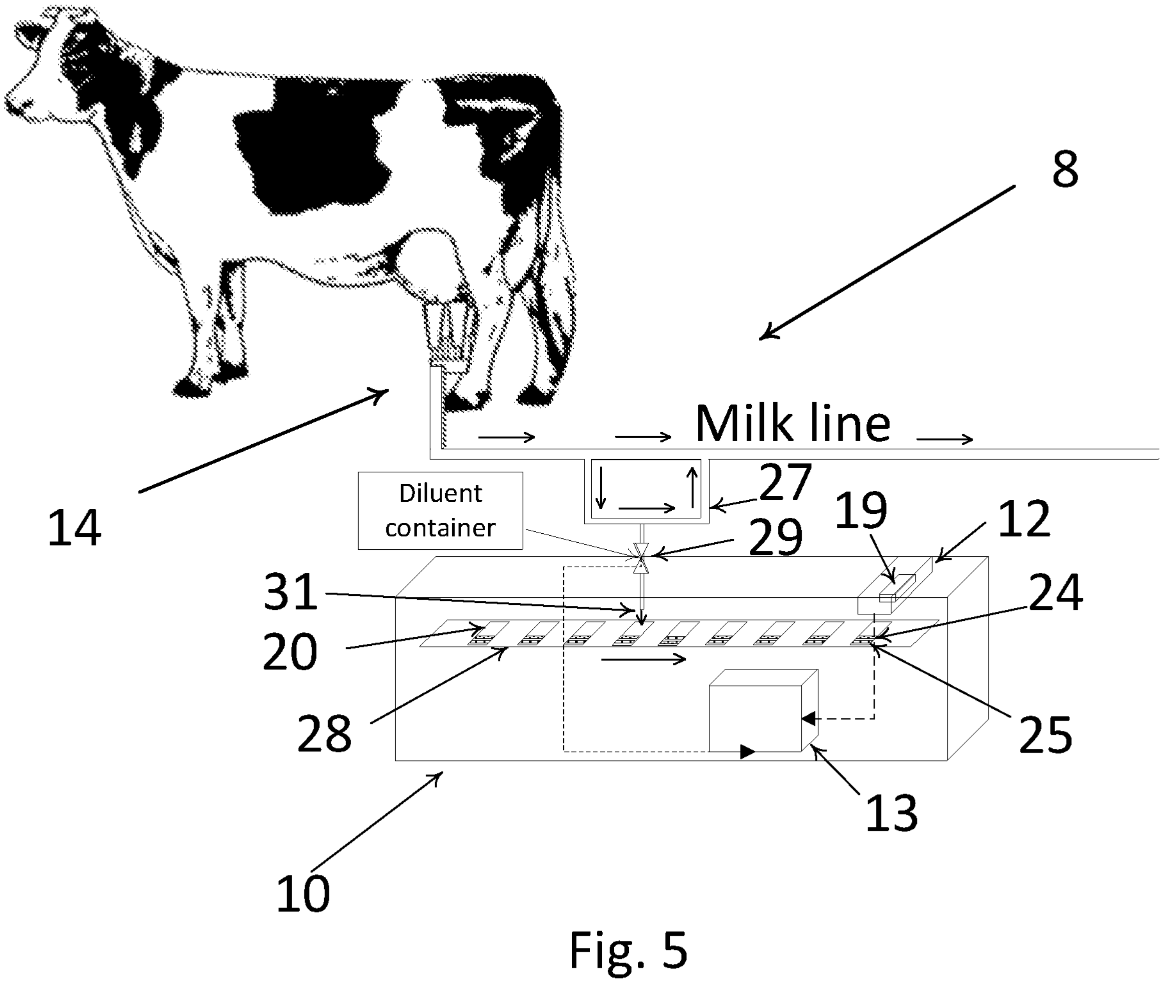

FIG. 5 schematically illustrates a milking arrangement according to another preferred embodiment of the invention. In FIG. 5, dotted lines indicates signals, such as control signal or read-out signals from sensors. As illustrated, the milking arrangement comprising milking machine 14 including teat cups attached to the udder of a cow for milking milk out of the udder. The teat cups are connected to a milk line configured to feed harvest milk into a receptacle (not illustrated). A sampling line 27 is fluidicly connected to the milk line to sample milk from the milk flowing in the milk line. In FIG. 5, the sampling line 27 is illustrated as bypass line with an electronically controlled valve 29. The sampling line 27, valve 29 and outlet 31 forms at least part of a sampling device.

The milking arrangement further comprises a conveyer 28 on which dry sticks 20 are placed and the conveyer conveys the dry sticks in a direction from left to right relatively to the orientation of FIG. 5.

An outlet 31 downstream of the valve 29 is arranged in close proximity to the conveyer 29 so that when a dry stick is conveyed to a position below the outlet 31, opening of the valve 29 provides one or more drops of milk to be applied to the dry stick 20. In a position away from the outlet 31, a haptoglobin sensor device 12 is arranged. In the disclosed embodiment, the haptoglobin sensor device 12 comprising the dry stick 20 and an optical device 19 comprising a camera device, which in the illustrated embodiment is a CCD camera, which is arranged to optically read the test signal, and if implemented, the control signal produced by the dry stick.

The milking arrangement comprises a processor 13. The processor 13 is configured to convert the signal(s) from the dry stick 20 (received from the haptoglobin sensor device 12) into a value of haptoglobin quantity in the milk sample. The processor 13 receives the signal from the sensor 12 typically as electrical signals as illustrated by the dotted lines in FIG. 5. The processor 13 is furthermore configured to control opening and closing of the valve 29 to allow milk to be applied to the dry stick 20. In addition, the processor is furthermore configured to control the movement of the conveyer 28 to advance dry sticks located on the conveyer 28 towards the outlet 31 providing milk and towards the CCD camera.

As can be readily understood, providing a distance between the position where the milk is applied to the dry stick and where the signal(s) produced by the dry stick is obtained by the CCD camera, represents a time during which the signal(s) can evolve on the dry stick(s). This time can be controlled by controlling the conveying speed, whereby the time during which the signal(s) evolves is controllable by the conveying speed. Thereby, if a certain amount of reaction time is aimed at, this may be accomplished by setting the conveying speed accordingly. However, it is to be emphasised that other ways of controlling the reaction time may be used. An alternative would be to arrange the CCD camera next to the outlet 31, typically with a field of view covering the position where the test line and the optional control line are located while the milk is applied to the dry stick. If longer incubation time is need and the dry stick has been moved past the field of view of the CCD camera, the conveyer may be reversed to move the stick backward to the reading position. This positioning of the CCD camera furthermore has the advantage that the application of milk to the dry stick may be monitored which may be used to assure that milk is intentionally and correctly applied to the dry stick.

In the disclosed embodiment of FIG. 5, the conveyer 20, the controller 13 and the haptoglobin sensor device 12 are illustrated as being contained in a physical delimited analysing unit 10, where the physical delimit is provided by a cabinet. By this, the interior of the cabinet may form an incubator where the atmosphere, such as humidity and/or temperature can be controlled.

FIG. 5 schematically illustrates an optional diluent container configured to contain a diluent to be added to the milk sample. The dosing of the milk sample and the diluent is provided one or more separate dosing pumps (not illustrated) being configured to dose diluent and milk typically simultaneous so as to obtain a correct, desired amount and diluent. The arrow in FIG. 5 from the diluent container to the valve schematically illustrates a flow of diluent.

Figure 2:
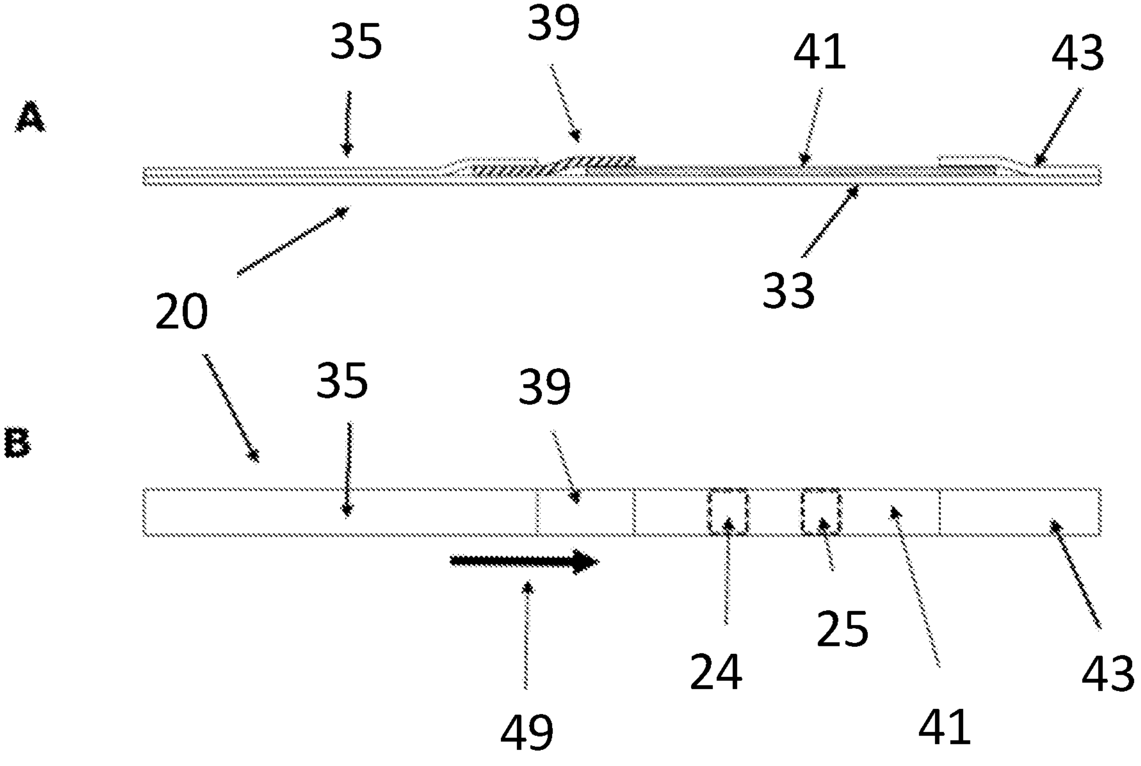
FIG. 2A-B schematically illustrates a dry stick used in connection with preferred embodiments of the present invention to determine a value of haptoglobin quantity.
Figure 3:
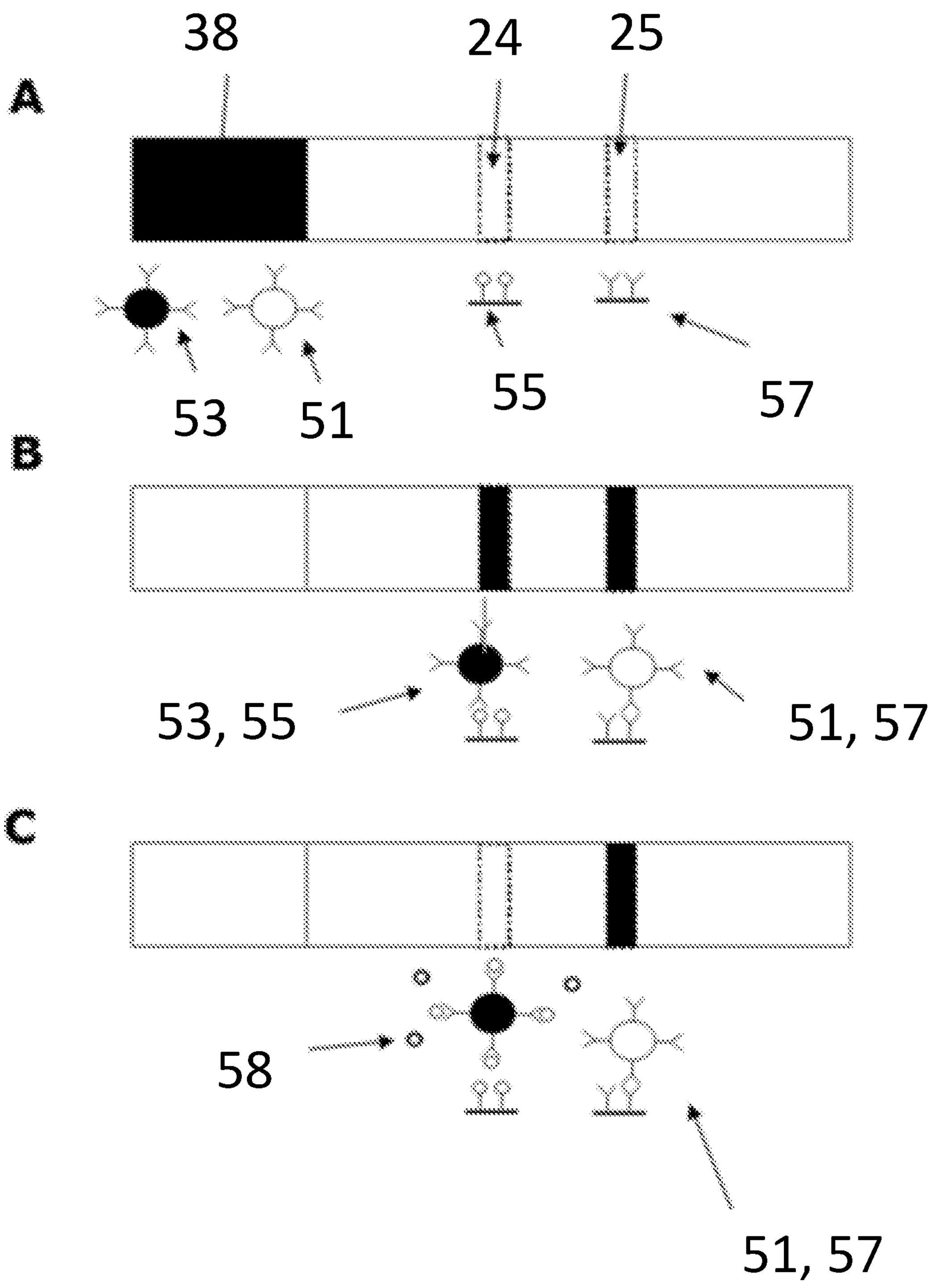
FIG. 3A-C show the principle of the dry stick used in connection with preferred embodiments of the present invention to determine a value of haptoglobin quantity.
Figure 6:
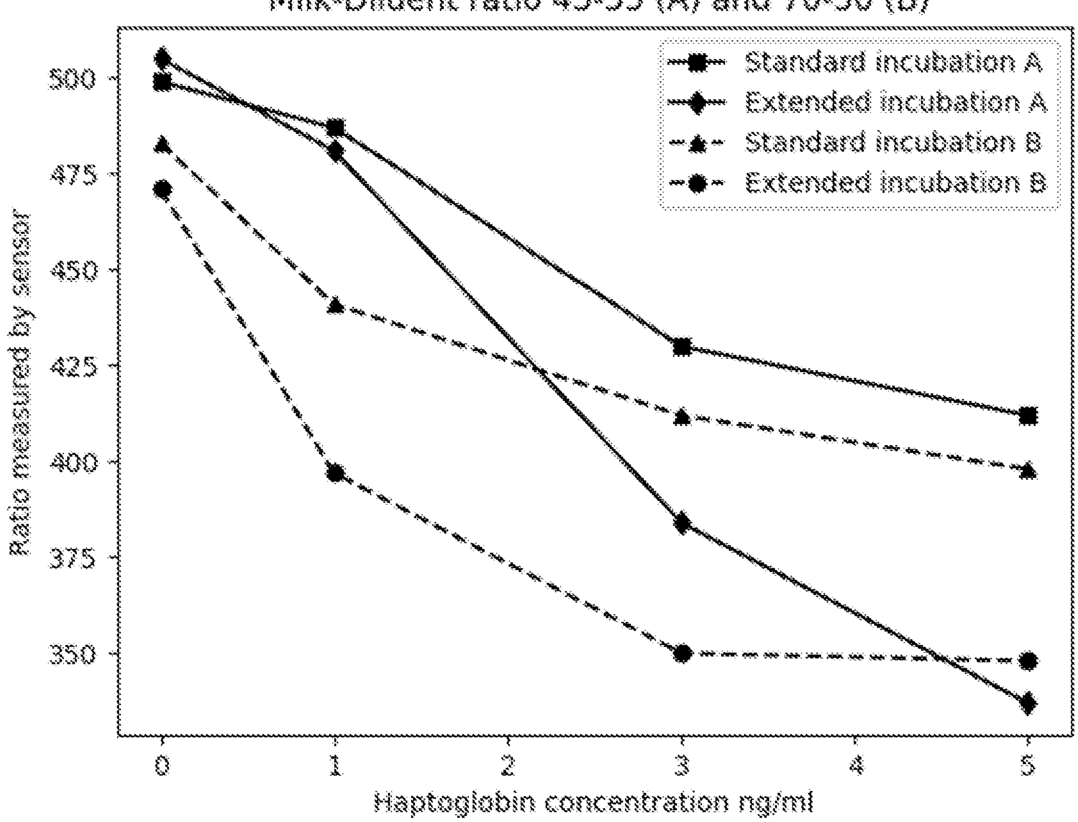
FIG. 6 illustrates experimental results for determination of haptoglobin in milk in accordance with the present invention.

Reference is made to FIG. 6 illustrating experimental data obtained with a dry stick as disclosed herein with reference to FIGS. 2 and 3. The experimental data is obtained by incubating the dry stick at two different incubation times labelled standard incubation time (5.5 minutes) and extended incubation time (11 minutes).

The experiments made are carried out to investigate sensitivity of the dry stick to very low haptoglobin concentrations in the milk sample and a number of test were carried out with different proportions between milk and diluent in the milk sample.

The hypotheses was that by increasing the proportion of milk in the milk sample the amount of actual haptoglobin present in the milk sample would increase, due to the reduced dilution of the milk sample.

Without being bound by theory, it is assumed that by increasing the proportion of milk in the milk sample the viscosity of the milk sample increases. The higher viscosity is suggested to cause the milk sample to flow slower down the dry stick.

A slower flow could potentially mean that a preset standard reaction time would not be sufficient for optimal reaction in the dry stick and hence it was tested if an increased incubation time would provide a more trustworthy signal from the dry stick.

The dry stick was tested with a standard incubation time of 5.5 minutes and with an extended incubation time of 11 minutes. However, it is to be noted that an optimal reaction time may be something in between these two times or greater than these times. The experiments were performed on a total milk sample volume (of each sample) of approx. 45 μl and with two different milk-dilutent proportions of (A) 45% milk and 55% diluent and (B) 70% milk and 30% diluent.

Increasing the incubation time resulted in a more trustworthy result, e.g. decreased ratio R(R is test signal/(test signal+control signal).

Thus, it was found that the effect of incubation time is also related to the milk-diluent proportion in the milk sample.

The graphs in FIG. 6 show the ratio on the y-axis, where the ratio is R=test signal/(test signal+control signal) and the x-axis shows the haptoglobin concentration. The graphs show different incubation times for different milk-diluent proportions. The graphs show that the effect of incubation time is greater for samples with a high proportion of milk.

In a preferred embodiment, this has been implemented a milking arrangement comprising a milking machine 14 for milking an animal, wherein the milking arrangement comprises an analysing unit 10 configured to determining a value of haptoglobin quantity in a milk sample taken from milk harvest by the milking machine 14, said analysing unit 10 comprising:

a haptoglobin sensor device 12 configured to provide a value of haptoglobin quantity 15 in said milk sample, and a processor 13, wherein said processor 13 being configured to assign the provided value of haptoglobin quantity to be a determined value of haptoglobin quantity when a reaction time, being a time during which said milk sample has been in contact with the haptoglobin sensor device, exceeds a total reaction time, wherein the total reaction time being determined on the basis of the amount of diluent added to said milk sample.

In certain preferred embodiments, the proportion of milk and diluent in the milk sample is selected in the range between 45% up to 85% milk and 55% down to 15% diluent, preferably the proportion of milk and diluent is selected as 45% milk and 55% diluent, preferably 55% milk and 45% diluent, preferably 70% milk and 30% diluent, preferably 85% milk and 15% diluent.

LIST OF REFERENCE SYMBOLS USED

8 Milking arrangement
10 Analysing unit
12 Haptoglobin sensor device
13 Processor
14 Milking machine
15 Value of haptoglobin quantity
16 Threshold time
17 Haptoglobin threshold
18 Elapsed reaction time
19 Optical device of haptoglobin sensor device
20 Dry stick
29 Valve
30 Incubator
31 Outlet
33 Backing card
35 Sample pad
37 Milk sample
39 Conjugate pad
41 Membrane
43 Absorbent pad
49 Lateral flow
51 Labelled-control conjugate
53 labelled-conjugate
55 Target analyte
57 Specific binding means
58 haptoglobin

The invention claimed is:

1. A milking arrangement comprising:

a milking machine (14) for milking an animal; and an analysing unit (10) configured to determine a value of haptoglobin quantity in a milk sample taken from milk harvest by the milking machine (14), said analysing unit (10) comprising:

a haptoglobin sensor device (12) configured to provide a value of haptoglobin quantity (15) in said milk sample, and a processor (13), wherein said processor (13) is configured, on the basis of a reaction time being a time during which said milk sample has been in contact with the haptoglobin sensor device, to:

determine, when the reaction time exceeds a threshold time (16), if the provided value of haptoglobin quantity is above a haptoglobin threshold (17), and in a confirmative case, assign the provided value of haptoglobin quantity to be a determined value of haptoglobin quantity, and in a non-confirmative case, increase the reaction time to a total reaction time, and at a point in time where the reaction time exceeds the total reaction time, provide a further value of the haptoglobin quantity in the milk sample and assign the provided further value of haptoglobin quantity to be the determined value of haptoglobin quantity.

2. The milking arrangement according to claim 1, further comprising a diluent container that uses a diluent to dilute the milk sample prior to being provided to the haptoglobin sensor device (12), wherein the haptoglobin sensor device (12) is configured to provide the value of haptoglobin quantity (15) in said milk sample having been diluted by the diluent, and the total reaction time is determined on the basis of an amount of the diluent added to the said milk sample.

3. The milking arrangement according to claim 2, wherein the proportion of milk and diluent in the milk sample is selected in a range between 45% up to 85% milk and 55% down to 15% diluent.

4. The milking arrangement according to claim 1, wherein the haptoglobin sensor device (12) comprising an optical device (19) configured to optically read:

a test signal at a test line of a dry stick (20), and wherein said processor (13) is configured to determine said provided value of haptoglobin quantity based on said test signal.

5. The milking arrangement according to claim 4, wherein the optical device (19) comprises a CCD-chip or a camera configured to optically read a colour intensity of the test line.

6. The milking arranged arrangement according to claim 5, wherein said processor is configured to determine the test signal on the basis of a colour intensity variation across the test line.

7. The milking arrangement according to claim 4, further comprising a first database look-up in a first database storing corresponding values of test signal, wherein said processor is configured to determine said provided value of haptoglobin quantity by a database look-up in the first database storing corresponding values of test signal.

8. The milking arrangement according to claim 1, wherein the haptoglobin sensor device (12) comprising an optical device (19) configured to optically read:

a test signal at a test line of a dry stick (20), and a control signal at a control line of said dry stick, wherein said processor is further configured to determine said provided value of haptoglobin quantity based on an algebraic relationship between the test signal and the control signal and haptoglobin quantity.

9. The milking arrangement according to claim 5, wherein said dry stick (20) comprises:

a base pad configured to allow lateral flow of fluid therethrough;

the base pad comprising a labelled-control conjugate and a labelled-conjugate diffusibly arranged herein, wherein said labelled-conjugate binds haptoglobin, and wherein a complex is formed between said labelled-conjugate and said haptoglobin when said dry stick is in use and said haptoglobin is present, wherein said base pad further comprises a test line comprising immobilised target analyte, wherein said immobilised target analyte binds to said labelled-conjugate when not in said complex; and a control line, which is spaced from said test line, and which comprises control analyte configured to bind to said labelled-control conjugate.

10. The milking arrangement according to claim 1, wherein the haptoglobin threshold is larger than 2.0 μg haptoglobin per ml milk and smaller than 20.0 μg haptoglobin per ml milk.

11. The milking arrangement according to claim 1, wherein the threshold time is larger than 3.0 minutes and smaller than 10 minutes and the total reaction time is less than 15.0 minutes.

12. The milking arrangement according to claim 1, wherein analysing unit is configured to:

digitally receive an identifier uniquely identifying a particular animal from which the milk sample is taken, digitally link the identifier and the determined value of haptoglobin quantity for the milk sample taken from said particular animal, and digitally output the linked identifier and determined value of haptoglobin quantity.

13. The milking arrangement according to claim 1, wherein the analysing unit (13) comprises a time counter configured to count the elapsed reaction time, and said processor (13) being configured to start the time counter when said processor (13) determines the point in time when the milk sample is applied to the haptoglobin sensor device (12).

14. The milking arrangement according to claim 1, wherein said processor (13) determines the point in time when the milk sample is applied to the haptoglobin sensor device (12) on the basis of a user input, or of a digital input to the processor (13), said digital input being generated as a result of a milk sample has been applied to the haptoglobin sensor device (12).

15. The milking arrangement according to claim 1, the milking arrangement further comprising a milking device (20) configured to milk the animal, and a sampling device fluidicly connected to milking device to sample the milk sample and apply at least a fraction of the milk sample to said haptoglobin sensor device (12).

16. A method of determining a haptoglobin quantity in a milk sample, the method being carried out by use of milking arrangement according to claim 1, and comprising:

obtaining the milk sample, applying the milk sample to the haptoglobin sensor device (12) and determining a point in time when the milk sample is applied to the haptoglobin sensor device (12), and determining, when the reaction time exceeds the threshold time, if the provided value of haptoglobin quantity is above the haptoglobin threshold, and in confirmative case, assign the provided value of haptoglobin quantity to be the determined value of haptoglobin quantity, and in non-confirmative case, increase the reaction time to the total reaction time and assign the further provided value of haptoglobin quantity to be determined value of haptoglobin quantity at the point in time where the reaction time exceeds the total reaction time.

17. The milking arrangement according to claim 15, further comprising:

a cabinet housing the haptoglobin sensor device, dry sticks, a conveyer located within the cabinet and on which the dry sticks are placed and moved, by the conveyer, in a first direction, the cabinet connected to the sampling device with the sampling device arranged to apply the at least a fraction of the milk sample to individual ones of the dry sticks on the conveyer for analysis by said haptoglobin sensor device within the cabinet.

18. The milking arrangement according to claim 17, wherein an interior of the cabinet forms a controlled-atmosphere incubator with at least one of humidity and temperature being controllable.

19. The milking arrangement according to claim 17, further comprising a diluent container that uses a diluent to dilute the milk sample prior to being provided to the haptoglobin sensor device (12), wherein the haptoglobin sensor device (12) is configured to provide the value of haptoglobin quantity (15) in said milk sample having been diluted by the diluent, and the total reaction time is determined on the basis of an amount of the diluent added to the said milk sample.

20. A milking arrangement comprising:

a milking machine (14) for milking an animal; and an analysing unit (10) configured to determining a value of haptoglobin quantity in a milk sample taken from milk harvest by the milking machine (14) and having been diluted by a diluent, said analysing unit (10) comprising:

a haptoglobin sensor device (12) configured to provide a value of haptoglobin quantity (15) in said milk sample, and a processor (13), wherein said processor (13) is configured to assign the provided value of haptoglobin quantity to be a determined value of haptoglobin quantity when a reaction time, being a time during which said milk sample has been in contact with the haptoglobin sensor device, exceeds a total reaction time, and wherein the total reaction time is determined on the basis of an amount of the diluent added to said milk sample.

* * * * *